(12) United States Patent
Maltz et al.

(10) Patent No.: US 11,875,430 B2
(45) Date of Patent: Jan. 16, 2024

(54) SYSTEM AND METHOD FOR SYNTHESIZING A PROJECTION IMAGE

(71) Applicant: SHANGHAI UNITED IMAGING HEALTHCARE CO., LTD., Shanghai (CN)

(72) Inventors: Jonathan Maltz, Houston, TX (US); Qi Yin, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 583 days.

(21) Appl. No.: 17/133,607

(22) Filed: Dec. 23, 2020

(65) Prior Publication Data

US 2021/0118201 A1 Apr. 22, 2021

Related U.S. Application Data

(63) Continuation of application No. PCT/CN2019/096372, filed on Jul. 17, 2019.

(51) Int. Cl.
  *G06T 11/00* (2006.01)
  *A61B 6/00* (2006.01)
  *G01N 23/04* (2018.01)

(52) U.S. Cl.
  CPC ............ *G06T 11/005* (2013.01); *A61B 6/482* (2013.01); *G01N 23/04* (2013.01); *G01N 2223/401* (2013.01); *G01N 2223/423* (2013.01)

(58) Field of Classification Search
  CPC ............. G06T 11/005; G06T 2211/408; G06T 3/4038; G06T 2207/10116;
  (Continued)

(56) References Cited

U.S. PATENT DOCUMENTS

2009/0087026 A1  4/2009  Xie et al.
2009/0297016 A1  12/2009  Levenson et al.
(Continued)

FOREIGN PATENT DOCUMENTS

CN    108957515 A    12/2018
WO    2014121072 A2    8/2014

OTHER PUBLICATIONS

International Search Report in PCT/CN2019/096372 dated Apr. 15, 2020, 6 Pages.
(Continued)

*Primary Examiner* — Molly Wilburn
(74) *Attorney, Agent, or Firm* — METIS IP LLC

(57) ABSTRACT

The present disclosure provides a method for synthesizing a projection image that represents a subject or object irradiated by X-rays from a radiation source. The method may include dividing an energy spectrum of the X-rays into one or more energy bins; determining a projection value of at least one pixel; determining a weighting coefficient corresponding to an energy bin based on a variation of the energy spectrum of the X-rays; and determining a weighted projection value of the at least one pixel based on the projection value of the at least one pixel and the weighting coefficient corresponding to the energy bin. The method may further include determining a pixel value of the at least one pixel based on the weighted projection values of the at least one pixel that correspond to all the one or more energy bins.

20 Claims, 14 Drawing Sheets

(58) Field of Classification Search
CPC . G06T 2207/20221; G06T 5/50; A61B 6/482; A61B 6/032; G01N 23/04; G01N 2223/401; G01N 2223/423
See application file for complete search history.

(56) References Cited

U.S. PATENT DOCUMENTS

| | | |
|---|---|---|
| 2010/0027743 A1 | 2/2010 | Engel et al. |
| 2012/0069953 A1 | 3/2012 | Chandra et al. |
| 2012/0263360 A1 | 10/2012 | Zhu et al. |
| 2018/0075627 A1 | 3/2018 | Bruder et al. |
| 2018/0209922 A1 | 7/2018 | Yamakawa et al. |
| 2018/0284035 A1 | 10/2018 | Steadman Booker et al. |
| 2018/0292332 A1 | 10/2018 | Yamakawa et al. |
| 2019/0043187 A1 | 2/2019 | Kuusela et al. |
| 2019/0080491 A1 | 3/2019 | Saito et al. |
| 2020/0193654 A1* | 6/2020 | Yanoff .................. A61B 6/4233 |
| 2022/0028127 A1* | 1/2022 | Daerr ................... A61B 6/4241 |

OTHER PUBLICATIONS

Written Opinion in PCT/CN2019/096372 dated Apr. 15, 2020, 4 Pages.

\* cited by examiner

500

| 502 | Dividing an energy spectrum of X-rays into one or more energy bins, the energy spectrum of the X-rays varying with respect to different regions of a projection image, each of the one or more energy bins corresponding to an energy range |

↓

| 504 | For at least one pixel of the projection image and for each energy bin of the one or more energy bins, determining a projection value of the at least one pixel indicating a transmission projection of X-rays corresponding to the at least one pixel and having an energy within the corresponding energy range of the energy bin |

↓

| 506 | Determining, for the at least one pixel, a weighting coefficient corresponding to the energy bin based on a variation of the energy spectrum of the X-rays between the different regions of the projection image |

↓

| 508 | Determining a weighted projection value of the at least one pixel based on the projection value of the at least one pixel and the weighting coefficient corresponding to the energy bin |

↓

| 510 | Determining a pixel value of the at least one pixel based on the weighted projection values of the at least one pixel that correspond to all of the one or more energy bins |

┌─────────────────────────────────────────────────────────────┐
│ Determining at least one distinctive energy spectrum that   │ 702
│ corresponds to at least one region of the projection image, the at │
│ least one distinctive energy spectrum includes a plurality of │
│ distinctive energy spectra corresponding to different regions of the │
│ projection image                                            │
└─────────────────────────────────────────────────────────────┘
                              ↓
┌─────────────────────────────────────────────────────────────┐
│ Determining a CDF for each of the plurality of distinctive energy │ 704
│ spectra, each CDF corresponding to one of the different regions of │
│ the projection image                                        │
└─────────────────────────────────────────────────────────────┘
                              ↓
┌─────────────────────────────────────────────────────────────┐
│ Determining an area of each of the different regions of the │ 706
│ projection image                                            │
└─────────────────────────────────────────────────────────────┘
                              ↓
┌─────────────────────────────────────────────────────────────┐
│ Weighting each of the plurality of CDFs by its corresponding area │ 708
└─────────────────────────────────────────────────────────────┘
                              ↓
┌─────────────────────────────────────────────────────────────┐
│ Determining the distribution of the energy spectrum based on the │ 710
│ weighted CDFs                                               │
└─────────────────────────────────────────────────────────────┘

FIG. 7

SYSTEM AND METHOD FOR SYNTHESIZING A PROJECTION IMAGE

CROSS-REFERENCE TO RELATED APPLICATIONS

This application is a continuation of International Application No. PCT/CN2019/096372 filed on Jul. 17, 2019, the entire contents of which are hereby incorporated by reference.

TECHNICAL FIELD

The present disclosure generally relates to systems and methods for synthesizing a projection image, and more particularly, to systems and methods for synthesizing a projection image generated from a radiation source with spatially-varying spectrum.

BACKGROUND

Synthetic projection images may have multiple applications in different fields, such as in radiology and radiation therapy. In the radiation therapy application, there may be a large variation in spectrum over the beam cross section. To reduce the influence caused by the variation, different regions of the image field may be projected separately. For example, a unique spectrum may be used to determine the projection within an annular ring of the image field, while causing sudden spectral transitions at boundaries between adjacent annular rings. Although thin annular rings may be further used to minimize those sudden spectral transitions, it may lower the computational efficiency for synthesizing the projection images. Therefore, it is desired to develop methods and systems for better synthesizing projection images from radiation source with spatially-varying spectrum.

SUMMARY

According to an aspect of the present disclosure, a method for synthesizing a projection image is provided. The projection image may represent a subject or object irradiated by X-rays from a radiation source. The method may include dividing an energy spectrum of the X-rays into one or more energy bins. The energy spectrum of the X-rays may vary with respect to different regions of the projection image. Each of the one or more energy bins may correspond to an energy range. The method may further include, for at least one pixel of the projection image, for each energy bin of the one or more energy bins, determining a projection value of the at least one pixel indicating a transmission projection of X-rays corresponding to the at least one pixel and having an energy within the corresponding energy range of the energy bin, determining a weighting coefficient corresponding to the energy bin based on a variation of the energy spectrum of the X-rays between the different regions of the projection image, and determining a weighted projection value of the at least one pixel based on the projection value of the at least one pixel and the weighting coefficient corresponding to the energy bin. And the method may further include determining a pixel value of the at least one pixel based on the weighted projection values of the at least one pixel that correspond to all of the one or more energy bins.

In some embodiments, dividing an energy spectrum of the X-rays into one or more energy bins may include determining a distribution of the energy spectrum that indicates a relationship between numbers of photons in the energy spectrum and energies in the energy spectrum, and dividing the energy spectrum into a plurality of energy bins based on the distribution of the energy spectrum such that each energy bin has an approximately identical number of photons within its corresponding energy range.

In some embodiments, determining a distribution of the energy spectrum that indicates a relationship between numbers of photons in the energy spectrum and energies in the energy spectrum may include determining at least one distinctive energy spectrum that corresponds to at least one region of the projection image, and determining the distribution of the energy spectrum based on a cumulative distribution function (CDF) of the at least one distinctive energy spectrum.

In some embodiments, the at least one distinctive energy spectrum may include a plurality of distinctive energy spectra corresponding to different regions of the projection image. Determining the distribution of the energy spectrum based on a cumulative distribution function (CDF) of the at least one distinctive energy spectrum may include determining a CDF for each of the plurality of distinctive energy spectra. Each CDF may correspond to one of the different regions of the projection image. And Determining the distribution of the energy spectrum based on a cumulative distribution function (CDF) of the at least one distinctive energy spectrum may further include determining the distribution of the energy spectrum based on an area-weighted mean of the plurality of CDFs corresponding to the plurality of distinctive energy spectra.

In some embodiments, determining the distribution of the energy spectrum based on an area-weighted mean of the plurality of CDFs corresponding to the plurality of distinctive energy spectra may include determining an area of each of the different regions of the projection image, weighting each of the plurality of CDFs by its corresponding area, and determining the distribution of the energy spectrum based on the weighted CDFs.

In some embodiments, determining an area of each of the different regions of the projection image may include determining a weighting factor for the each of the different regions of the projection image, determining an actual area for the each of the different regions of the projection image, and determining the area of the each of the different regions of the projection image based on the weighting factor for the each of the different regions of the projection image and the actual area for the each of the different regions of the projection image.

In some embodiments, determining a projection value of the at least one pixel indicating a transmission projection of X-rays corresponding to the at least one pixel and having an energy within the corresponding energy range of the energy bin may include determining a line integral of an attenuation coefficient along a direction of the X-rays corresponding to the at least one pixel and having the energy within the corresponding energy range of the energy bin.

In some embodiments, the attenuation coefficient may correspond to an average energy of the energy bin.

In some embodiments, determining a weighting coefficient corresponding to the energy bin based on a variation of the energy spectrum of the X-rays with respect to the different regions of the projection image may include determining a position of the at least one pixel in the projection image, determining a relationship between positions of pixels in the projection image and weighting coefficients corresponding to the energy bin, and determining the weighting coefficient corresponding to the energy bin based on the position of the at least one pixel in the projection image and the relationship.

In some embodiments, a position of a pixel in the projection image may include a radial distance of the at least one pixel with respect to a center of the projection image.

In some embodiments, the method may further include determining, for each of the different regions of the projection image, a representative weighting coefficient corresponding to the energy bin. And the method may also include determining a function by fitting the representative weighting coefficients of the different regions of the projection image.

In some embodiments, the representative weighting coefficient corresponding to the energy bin for each of the different regions of the projection image may relate to a count of photons that are within the energy range of the energy bin and correspond to the each of the different regions of the projection image.

In some embodiments, the relationship may be such that the weighting coefficients corresponding to the energy bin change continuously with respect to the positions of the pixels in the projection image.

In some embodiments, the weighting coefficient corresponding to each energy bin may be a weighting of a basis set that approximates the spectrum of the X-rays over the projection image.

According to an aspect of the present disclosure, a system for synthesizing a projection image is provided. The system may include at least one storage medium including a set of instructions and at least one processor in communication with the at least one storage medium. When executing the instructions, the at least one processor may be configured to direct the system to perform operations. The operations may include dividing an energy spectrum of the X-rays into one or more energy bins. The energy spectrum of the X-rays may vary with respect to different regions of the projection image. Each of the one or more energy bins may correspond to an energy range. The operations may further include, for at least one pixel of the projection image, for each energy bin of the one or more energy bins, determining a projection value of the at least one pixel indicating a transmission projection of X-rays corresponding to the at least one pixel and having an energy within the corresponding energy range of the energy bin, determining a weighting coefficient corresponding to the energy bin based on a variation of the energy spectrum of the X-rays between the different regions of the projection image, and determining a weighted projection value of the at least one pixel based on the projection value of the at least one pixel and the weighting coefficient corresponding to the energy bin. And the operations may also include determining a pixel value of the at least one pixel based on the weighted projection values of the at least one pixel that correspond to all of the one or more energy bins.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5 is a flowchart illustrating an exemplary process for synthesizing a projection image according to some embodiments of the present disclosure;

FIG. 7 is a flowchart illustrating an exemplary process for determining a distribution of energy spectrum according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
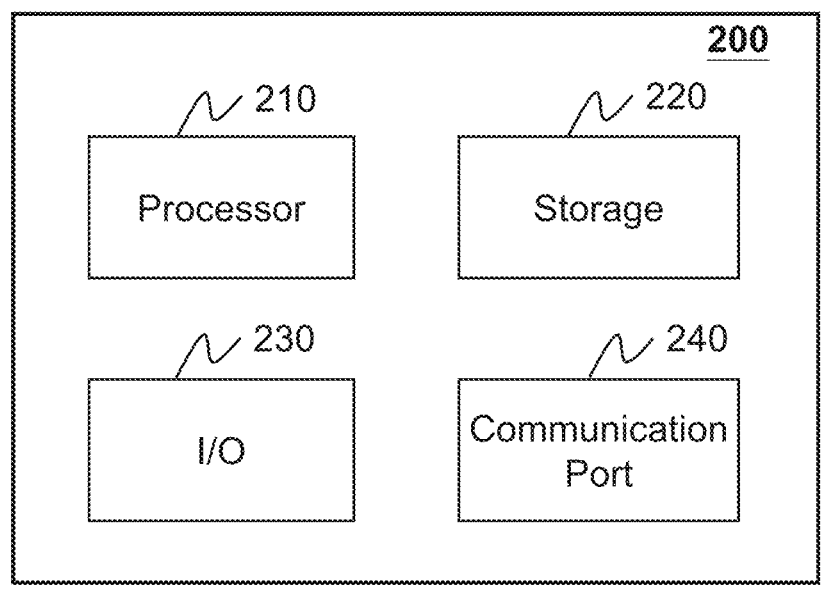
FIG. 2 is a schematic diagram illustrating an exemplary computing device on which at least a portion of the imaging system 100 can be implemented, according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when as used herein, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and methods for imaging, such as for disease diagnosis, physical check-up, or disease treatment. For example, the imaging systems and methods provided in the present disclosure may be used in an internal inspection (e.g., a non-invasive internal inspection) including, for the anatomical structure of one or more tissues or one or more organs, the metabolism of one or more tissues or one or more organs, the function of one or more tissues or one or more organs. The imaging system may find its applications in different fields other than the medical fields. For example, the imaging system may be used in an internal inspection (e.g., a non-invasive internal inspection) of one or more components. For example, the imaging systems and methods provided in the present disclosure may be used in flaw detection of a component of a machine, bag or luggage security scanning, failure analysis, metrology, assembly analysis, void detection, wall thickness assessment, or the like, or any combination thereof.

Some embodiments of the present disclosure provide systems and methods for synthesizing a projection image. In some embodiments, the synthetic projection images may be used for synthesis of digitally-reconstructed radiographs, which provide two-dimensional (2D) representations of attenuation within a three-dimensional (3D) image volume along a certain view direction. In some embodiments, the synthetic projection images may be used for synthesis of portal images in radiation therapy, which may be used for visualization, position verification and portal dosimetry. For example, synthesized portal images may be compared to identify and compare, between image pairs, the absolute and relative positions of anatomical features, fiducial markers, and treatment fields. For another example, the synthesized portal images may be compared to a 2D distribution derived from a treatment plan to perform verification of aspects of a treatment delivery. Specifically, a projection image may be synthesized from a treatment image and then compared to an image synthesized from a planning CT image. The projection image may be a standard radiographic projection, a 2D dose distribution, or a dose quality metric such as gamma index map.

In some embodiments, to synthesize the projection image with a high quality, the spatially-varying spectrum of the radiation source (e.g., an X-ray source) may be taken into account. Specifically, the spatially-varying spectrum of the X-rays may be divided into one or more energy bins, and the spatial variation of the spectrum may be represented by spatially-varying weighting coefficients for each energy bin. Accordingly, for each pixel of the projection image, the pixel value may be determined based on the transmission projection of X-rays corresponding to each energy bin, and the weighting coefficient corresponding to each energy bin and the spatial position of the pixel.

The following description is provided to facilitate better understanding of projection image synthesis methods and/or systems. The term "image" used in this disclosure may refer to a 2D image, a 3D image, a 4D image, and/or any related image data (e.g., projection data and/or corresponding image data). The image data may correspond to a distribution of the degree of absorption of X-ray beams by different anatomical structures of a subject (e.g., a patient) or an object. The projection data corresponding to the image data may refer to a sum or line integral of linear attenuation coefficient(s) along a plurality of X-ray beam directions.

The following descriptions in connection with a CT imaging system are provided for illustration purposes. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Figure 1:
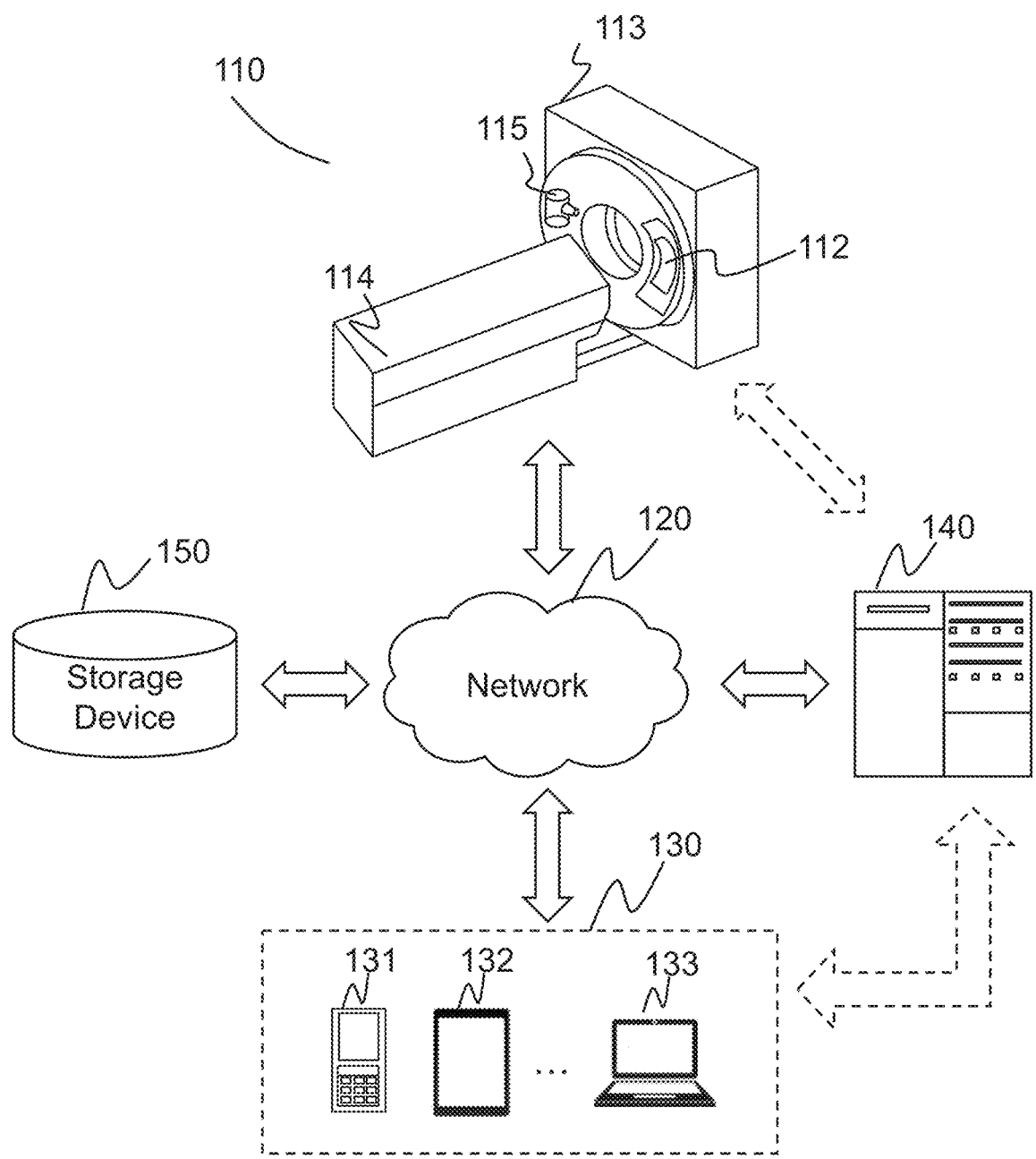
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. The imaging system 100 may include an imaging devices 110, a network 120, one or more terminals 130, a processing device 140, and a storage device 150.

The imaging devices 110 may be a computed tomography (CT) imaging device, a magnetic resonance image (MRI) device, or a positron-emission tomography (PET) imaging device, etc. The imaging device 110 may include a gantry 113, a detector 112, a table 114, and a scanning source 115. The gantry 113 may support the detector 112 and the scanning source 115. A subject (or an object) may be placed on the table 114 for scanning. The scanning source 115 may emit X-rays to the subject. The detector 112 may detect attenuated X-rays. The attenuated X-rays may further be processed and converted to image data for image reconstruction. Merely by way of example with reference to the imaging system 100, the X-rays may be generated by the scanning source 115 according to the bremsstrahlung principle, and an energy spectrum of the X-rays may be varying over the spatial positions. The detector 112 may include a semiconductor detector, a gas detector, or a scintillation detector, etc. In some embodiments, the detector 112 may include a plurality of detector units, and the plurality of detector units may be arranged in any suitable manner. For example, the plurality of detector units may be arranged on a plane, and the detector 112 may be a flat panel detector. As another example, the plurality of detector units may be arranged on an arc surface, and the detector 112 may be an arc-shaped detector.

In some embodiments, a treatment device (not shown in the figure) may be added to the imaging system 100. The treatment device may include a treatment radiation source, a gantry, a collimator, or the like, or a combination thereof. The treatment radiation source may be a linear accelerator (LINAC). The collimator may control the shape of the radioactive rays generated by the treatment radiation source. In some embodiments, the imaging device 110 and the treatment device may share a same gantry. For example, the treatment radiation source may be mounted on the gantry 113. A subject may be placed on the table 114 for treatment and/or scan. Merely by way of example with reference to a radiation therapy device, the imaging system 100 may be an RT-CT system. The imaging device 110 described herein may be applied in subject positioning and/or verification in image-guided radiation therapy (IGRT). The image for guiding a radiation therapy may be generated based on the image data processed/converted from the attenuated X-rays detected by the detector 112 of the imaging device 110.

The network 120 may include any suitable network that can facilitate the exchange of information and/or data for the imaging system 100. In some embodiments, one or more components of the imaging system 100 (e.g., the imaging device 110, the terminal(s) 130, the processing device 140, the storage device 150, etc.) may exchange information and/or data with one or more other components of the imaging system 100, or an external device (e.g., an external storage device) via the network 120. For example, the processing device 140 may obtain projection data from the imaging device 110 via the network 120. As another example, the processing device 140 may obtain user instructions from the terminal(s) 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 702.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

Figure 3:
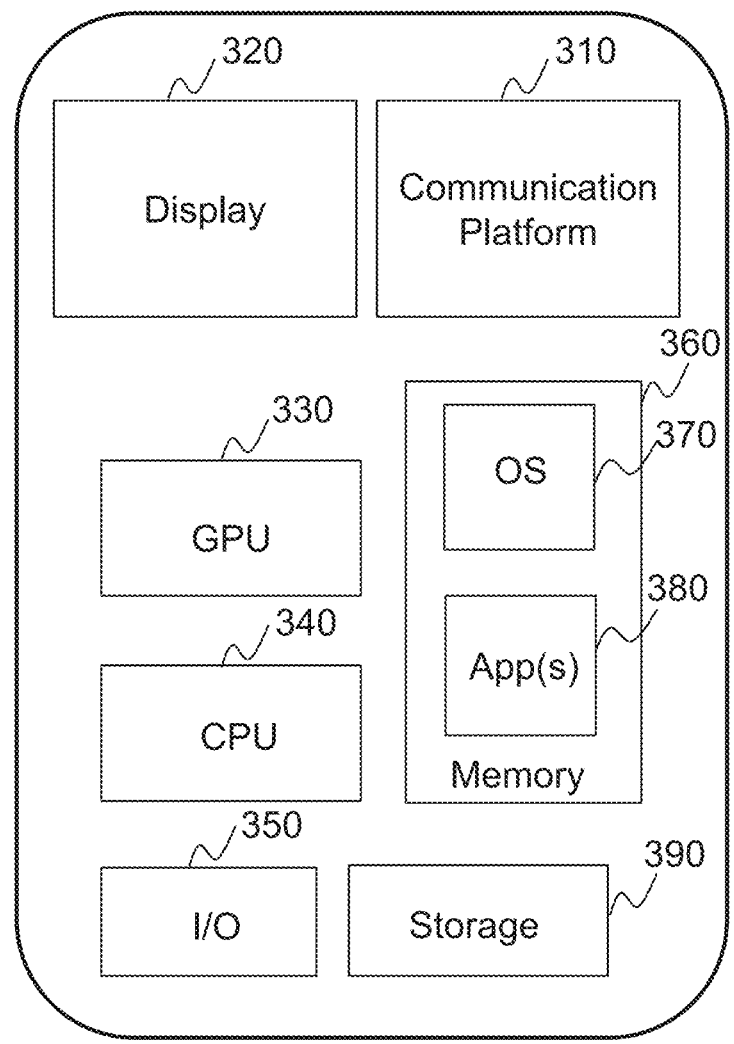
FIG. 3 is a schematic diagram illustrating hardware and/or software components of an exemplary mobile device according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data, images, and/or information obtained from the imaging device 110, the terminal(s) 130, the storage device 150, an external device, etc. In some embodiments, the processing device 140 may be a single server or a server group. The server group may be centralized or distributed. In some embodiments, the processing device 140 may be local to or remote from other components of the imaging system 100 (e.g., the imaging device 110). For example, the processing device 140 may access, via the network 120, data, images, and/or information stored in the imaging device 110, the terminal(s) 130, the storage device 150, an external device, etc. As another example, the processing device 140 may be directly connected to the imaging device 110, the terminal(s) 130, and/or the storage device 150 to access stored data, images, and/or information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be directly connected to or communicate with one or more other components of the imaging system 100 (e.g., the processing device 140, the terminal(s) 130). In some embodiments, the storage device 150 may be part of the processing device 140.

FIG. 2 is a schematic diagram illustrating an exemplary computing device 200 on which at least a portion of the imaging system 100 can be implemented, according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process projection data obtained from the imaging device 110, the terminal(s) 130, the storage device 150, and/or any other component of the imaging system 100. As another example, the processor 210 may process image(s) obtained from the terminal(s) 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus, operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 130, the storage device 150, and/or any other component of the imaging system 100, an external device, etc. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for synthesizing a projection image.

The I/O 230 may input and/or output signals, data, information, etc. In some embodiments, the I/O 230 may enable user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the imaging device 110, the terminal(s) 130, and/or the storage device 150. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal(s) 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
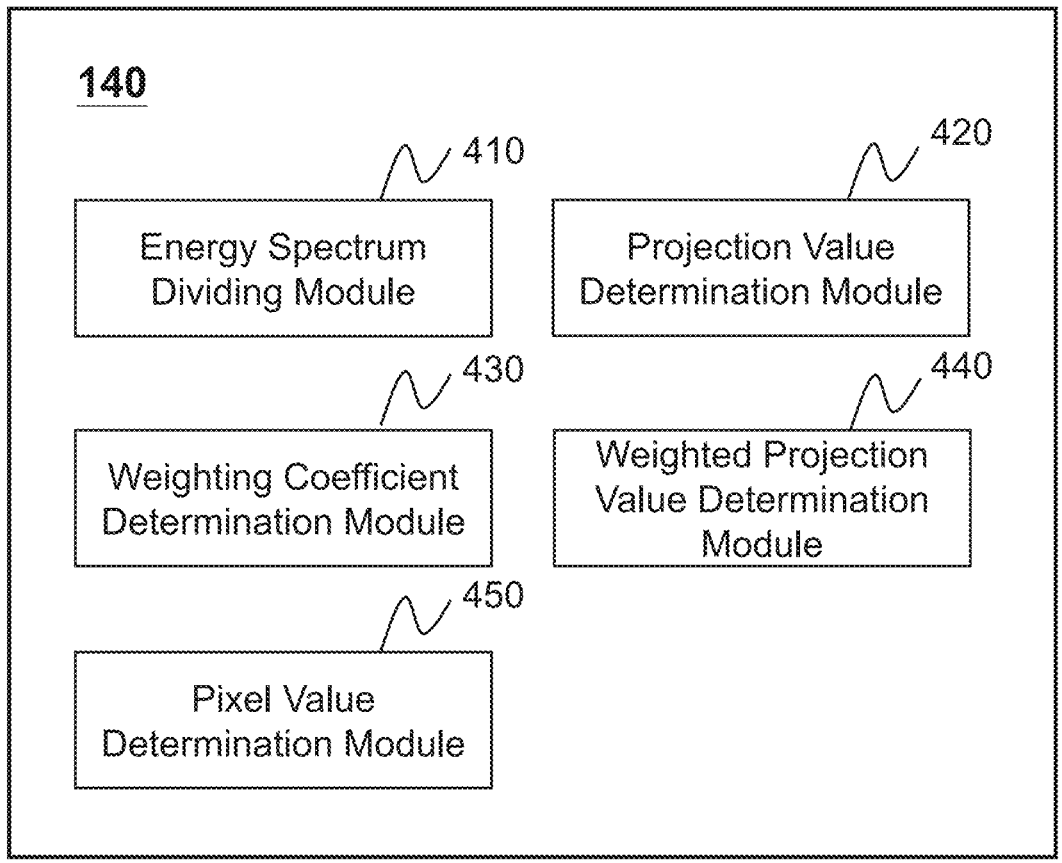
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include an energy spectrum dividing module 410, a projection value determination module 420, a weighting coefficient determination module 430, a weighted projection value determination module 440, a pixel value determination module 450. The processing device 140 may be implemented on various components (e.g., the computing device 200 as illustrated in FIG. 2, the mobile device 300 as illustrated in FIG. 3).

The energy spectrum dividing module 410 may be configured to divide an energy spectrum of X-rays into one or more energy bins. In some embodiments, the X-rays may pass through a subject to produce a projection image of the subject. The energy spectrum of the X-rays entering the subject may represent a distribution of the photons with respect to different energies. The energy spectrum of the X-rays entering the subject may vary over the spatial positions, e.g., over the beam cross section of the X-rays, or over different regions of the projection image.

In some embodiments, to divide an energy spectrum of X-rays into one or more energy bins, the energy spectrum dividing module 410 may be configured to determine a distribution of the energy spectrum of the X-rays that indicates a relationship between numbers of photons in the energy spectrum and energies in the energy spectrum. Specifically, the energy spectrum dividing module 410 may determine, from the spatially-varying energy spectrum of the X-rays, at least one distinctive energy spectrum that corresponds to at least one region of the projection image, determine a CDF for each of the plurality of distinctive energy spectra, each CDF corresponding to one of the different regions of the projection image, determine an area of each of the different regions of the projection image, weight each of the plurality of CDFs by its corresponding area, and determine the distribution of the energy spectrum based on the weighted CDFs. In some embodiments, to determine an area of each of the different regions of the projection image, the energy spectrum dividing module 410 may be configured to determine a weighting factor for each of the different regions of a projection image, determine an actual area for each of the different regions of the projection image, and determine the area of each of the different regions of the projection image based on the weighting factor for the each of the different regions of the projection image and the actual area for the each of the different regions of the projection image. In some embodiments, the energy spectrum dividing module 410 may be further configured to divide, based on the distribution of the energy spectrum, the energy spectrum into a plurality of energy bins such that each energy bin has an identical or approximately identical number of photons within its corresponding energy range.

The projection value determination module 420 may be configured to, for at least one pixel of the projection image and for each energy bin of the one or more energy bins, determine a projection value of the at least one pixel indicating a transmission projection of X-rays corresponding to the at least one pixel and having an energy within the corresponding energy range of the energy bin. In some embodiments, the projection value of one or more pixels may relate to the capability of the subject for attenuating the X-rays passing through it. In some embodiments, the capability of the subject for attenuating the X-rays may be represented by an attenuation coefficient. In some embodiments, to determine a projection value of the at least one pixel of the projection image, the projection value determination module 420 may be configured to calculate a sum or line integral of the attenuation coefficient along a direction of the X-rays that points from the radiation source to the at least one pixel.

The weighting coefficient determination module 430 may be configured to determine, for the at least one pixel, a weighting coefficient corresponding to the energy bin based on a variation of the energy spectrum of the X-rays between the different regions of the projection image. The weighting coefficient corresponding to the energy bin may provide a weight to the projection value corresponding to the energy bin. In some embodiments, the spectrum of the X-rays over the projection image (or a region of interest in the projection image) may be approximated by a basis set, and the weighting coefficient corresponding to each energy bin may be a weighting of the basis set.

In some embodiments, the weighting coefficient determination module 430 may be configured to determine a position of the at least one pixel in the projection image. A position of a pixel in the projection image may include a radial distance of the at least one pixel with respect to a center of the projection image. In some embodiments, the weighting coefficient determination module 430 may be further configured to determine, for each energy bin, a relationship between positions of pixels in the projection image and weighting coefficients. In some embodiments, the relationship between positions of pixels in the projection image and weighting coefficients may be represented by a specific function. In some embodiments, for each energy bin, to determine the relationship between positions of pixels in the projection image and weighting coefficients, the weighting coefficient determination module 430 may determine a representative weighting coefficient corresponding to the energy bin for each of the different regions of the projection image. For each of the different regions of the projection image, its representative weighting coefficient may relate to the count of photons that are within the energy range of the energy bin. And the the weighting coefficient determination module 430 may further determine a function by fitting the representative weighting coefficients of the different regions of the projection image. In some embodiments, the weighting coefficient determination module 430 may be further configured to determine the weighting coefficient corresponding to the energy bin based on the position of the at least one pixel in the projection image and the relationship.

The weighted projection value determination module 440 may be configured to determine a weighted projection value of the at least one pixel based on the projection value of the at least one pixel and the weighting coefficient corresponding to the energy bin. In some embodiments, The weighted projection value determination module 440 may be configured to multiply a projection value by a weighting coefficient to determine a weighted projection value.

The pixel value determination module 450 may be configured to determine a pixel value of the at least one pixel based on the weighted projection values of the at least one pixel that correspond to all of the one or more energy bins.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. Merely by way of example, the processing device 140 may include one or more other modules. However, those variations and modifications also fall within the scope of the present disclosure.

FIG. 5 is a flowchart illustrating an exemplary process 500 for synthesizing a projection image according to some embodiments of the present disclosure. In some embodiments, at least part of the process 500 may be performed by the processing device 140 (implemented in, for example, the computing device 200 shown in FIG. 2). For example, the process 500 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order of the operations of the process 500 as illustrated in FIG. 5 and described below is not intended to be limiting.

In 502, the processing device 140 (e.g., the energy spectrum dividing module 410) may divide an energy spectrum of X-rays into one or more energy bins. In some embodiments, the X-rays may pass through a subject to produce a projection image of the subject. The energy spectrum of the X-rays entering the subject may represent a distribution of the photons with respect to different energies. The energy spectrum of the X-rays entering the subject may vary over the spatial positions, e.g., over the beam cross section of the X-rays, or over different regions of the projection image.

In some embodiments, the X-rays may be generated by the scanning source 115 in the imaging device 110 according to a certain principle (e.g., the Bremsstrahlung principle). For example, the scanning source 115 may include an X-ray tube which may generate X-rays with a power supply provided by a high voltage generator. Specifically, the X-ray tube may at least include an anode and a cathode. The cathode may include one or more filaments (e.g., a tungsten wire, an iridium wire, a nickel wire, a molybdenum wire) configured to emit free electrons. The free electrons may be accelerated in an electric field between the cathode and the anode to form an electron beam striking the anode to further generate radioactive rays such as X-rays. The anode may be made of an electrically conductive material, and may have a high mechanical strength under a high temperature and have a high melting point. Exemplary materials may include titanium zirconium molybdenum (TZM), ferrum, cuprum, tungsten, graphite, or the like, or an alloy thereof, or any combination thereof.

In some embodiments, the projection image may be obtained by performing a scan of the subject or a portion thereof using the imaging device 110. For example, the scanning source 115 may emit the X-rays to scan the subject or a portion thereof (e.g., the head, a breast, etc., of a patient) located on the table 114. The detector 112 may detect one or more X-rays emitted from the scanning source 115 or scattered by the subject or a portion thereof to obtain projection values. The projection values may be transmitted to the processing device 140 for generating the projection image. In some embodiments, the processing device 140 may further reconstruct an image of the subject or a portion thereof based on the projection values using a reconstruction algorithm. Exemplary reconstruction algorithms may include an iterative reconstruction algorithm (e.g., a statistical reconstruction algorithm), a Fourier slice theorem algorithm, a fan-beam reconstruction algorithm, an analytic reconstruction algorithm, an algebraic reconstruction technique (ART), a simultaneous algebra reconstruction technique (SART), a filtered back projection (FBP) technique, a Feldkamp-Davis-Kress (FDK) reconstruction technique, or the like, or any combination thereof.

In some embodiments, different regions of the projection image may be radiated by different portions of the X-rays that have different energy spectra. For brevity, if a specific region of the projection image is radiated by a portion of the X-rays, the portion of the X-rays may be referred to as the corresponding X-rays of the specific region. In certain embodiments, the projection image may be divided into two or more regions. For each of the two or more regions, the energy spectrum of the corresponding X-rays may be deemed to be uniform in the condition that the variation of the energy spectrum of the corresponding X-rays is below a threshold. Merely by way of example, in the condition that the X-rays are radially symmetric (e.g., the X-rays form a cone beam), the region of the projection image may be divided into two or more annular rings. The energy spectrum corresponding to each of the two or more annular rings of the projection image may be deemed to be uniform, and the energy spectra of the X-rays corresponding to different annular rings of the projection image may be deemed to be different. For brevity, the energy spectrum that corresponds to a specific region of the projection image and is deemed uniform may be referred to as a distinctive energy spectrum.

In some embodiments, the spatially-varying energy spectrum may be divided into one or more energy bins such that the attenuation of the X-rays corresponding to each of the one or more energy bins may be determined, respectively. Each of the one or more energy bins may be delimited by two energy limits (i.e., an upper energy limit and a lower energy limit), and have an energy range within the two energy limits. For example, an energy spectrum of X-rays may be divided into N energy bins, which are delimited by energy limits $E_0, E_1, \ldots, E_N$, wherein $E_n > E_{n-1}$. It shall be noted that the division of the energy bins may be realized according to a specific rule. For example, the specific rule may be that the divided energy bins have an identical energy range, or the number of photons within each of the divided energy bins may be identical, or the like. More descriptions regarding the division of the energy bins may be found elsewhere in the present disclosure. See, e.g., FIG. 6 and the descriptions thereof.

In 504, for at least one pixel of the projection image and for each energy bin of the one or more energy bins, the processing device 140 (e.g., the projection value determination module 420) may determine a projection value of the at least one pixel indicating a transmission projection of X-rays corresponding to the at least one pixel and having an energy within the corresponding energy range of the energy bin.

In some embodiments, the projection value of one or more pixels may relate to the capability of the subject for attenuating the X-rays passing through it. For example, with a higher capability of attenuating the X-rays, the subject may be more likely to absorb or scatter the X-rays, thus producing a smaller projection value of the one or more pixels. With a lower capability of attenuating the X-rays, the subject may be less likely to absorb or scatter the X-rays, thus producing a larger projection value of the one or more pixels. Additionally, in some embodiments, the projection value of one or more pixels may relate to the energy of the X-rays passing through the subject. The X-rays with different energies may be attenuated non-uniformly when passing through the subject. The lower energy X-rays may be attenuated more when travelling through a dense part (a part with a higher density) of the subject.

In some embodiments, the capability of the subject for attenuating the X-rays may be represented by an attenuation coefficient. To determine a projection value of the at least one pixel of the projection image, the processing device 140 (e.g., the projection value determination module 420) may calculate a sum or line integral of the attenuation coefficient along a direction of the X-rays that points from the radiation source to the at least one pixel. As described above, the attenuation coefficient may depend on the energy of the X-rays. In some embodiments, for simplicity, the attenuation coefficients corresponding to different energies of the X-rays that are within one energy bin as described above may share a same attenuation value. The same attenuation value may be the value of the attenuation coefficient corresponding to an energy typical of the energy bin (e.g., an average energy of the energy bin, the upper energy limit of the energy bin, the lower energy limit of the energy bin).

For illustration purpose, an exemplary projection value of a pixel for an energy bin may be derived from a continuous transmission projection as follows:

$$P_n(m) = e^{\int dl \mu(X, (E_n + E_{n-1})/2)}, \quad (1)$$

where m denotes a continuous position on a detector (e.g., the detector 112), l denotes the line connecting the radiation source and the position m, X denotes a position within the subject that is passed by the X-rays, n denotes the series number of the energy bin, and μ denotes the attenuation coefficient of the subject, which relates to the average energy $(E_n + E_{n-1})/2$ of the energy bin.

In some embodiments, if the projection image has a rectangular pixel, an exemplary projection value of a pixel for an energy bin may be expressed as:

$$P_n[u, v] = \int dm_1 \int dm_2 P_n(m_1, m_2) \delta(m_1 - u\Delta m_1, m_2 - v\Delta m_2), \quad (2)$$

where $P_n[u, v]$ is the projection value of a pixel with a coordinate [u, v] on the detector 112, and Δm denotes side widths of the rectangular pixel.

In some embodiments, the projection value may be pre-processed before further processing (e.g., determining the pixel value of the pixel). For example, the processing device 140 (e.g., the projection value determination module 420) may eliminate or reduce errors and/or influences caused by physical factors on the projection value. Exemplary preprocessing operations may include air correction, crosstalk correction, off-focal correction, beam hardening correction, or the like, or any combination thereof.

In 506, the processing device 140 (e.g., the weighting coefficient determination module 430) may determine, for the at least one pixel, a weighting coefficient corresponding to the energy bin based on a variation of the energy spectrum of the X-rays between the different regions of the projection image. The weighting coefficient corresponding to the energy bin may provide a weight to the projection value corresponding to the energy bin. In some embodiments, for a specific pixel, different projection values corresponding to different energy bins may be provided with different weights.

In some embodiments, the processing device 140 (e.g., the weighting coefficient determination module 430) may determine a position of the at least one pixel in the projection image, and acquire a relationship between positions of pixels in the projection image and weighting coefficients corresponding to the energy bin. In some embodiments, the position of the at least one pixel in the projection image may include a radial distance of the at least one pixel with respect to a center of the projection image. The processing device 140 (e.g., the weighting coefficient determination module 430) may further determine the weighting coefficient corresponding to the energy bin based on the position of the at least one pixel in the projection image and the relationship.

In some embodiments, for a specific pixel, the weighting coefficient corresponding to the energy bin may be related to a count of photons that are within the energy range of the energy bin and correspond to the region of the projection image to which the photons are emitted. More descriptions regarding the weighting coefficients may be found elsewhere in the present disclosure. See, e.g., FIG. 9 and the descriptions thereof.

In 508, the processing device 140 (e.g., the weighted projection value determination module 440) may determine a weighted projection value of the at least one pixel based on the projection value of the at least one pixel and the weighting coefficient corresponding to the energy bin.

In some embodiments, a projection value may be multiplied by a weighting coefficient to determine a weighted projection value. For example, if the projection value of a pixel at position [u, v] on the detector 112 and corresponding to the nth energy bin is $P_n[u, v]$, and the weighting coefficient of the at least one pixel at the position [u, v] on the detector 112 and corresponding to the nth energy bin is $\omega_n[u, v]$, the corresponding weighted projection value may be expressed as $\omega_n[u, v]P_n[u, v]$.

In 510, the processing device 140 (e.g., the pixel value determination module 450) may determine a pixel value of the at least one pixel based on the weighted projection values of the at least one pixel that correspond to all of the one or more energy bins.

In some embodiments, the processing device 140 (e.g., the pixel value determination module 450) may determine a pixel value of the at least one pixel by summing up the weighted projection values of the at least one pixel that correspond to all of the one or more energy bins based on following formula:

$$P[u,v]=\Sum_{n=1}^{N}\omega_n[u,v]P_n[u,v], \quad (3)$$

where P[u, v] denotes the pixel value of the at least one pixel, and N is the total number of energy bins.

It should be noted that the above descriptions of the process 500 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 500 may include one or more other operations. However, those variations and modifications also fall within the scope of the present disclosure.

Figure 6:
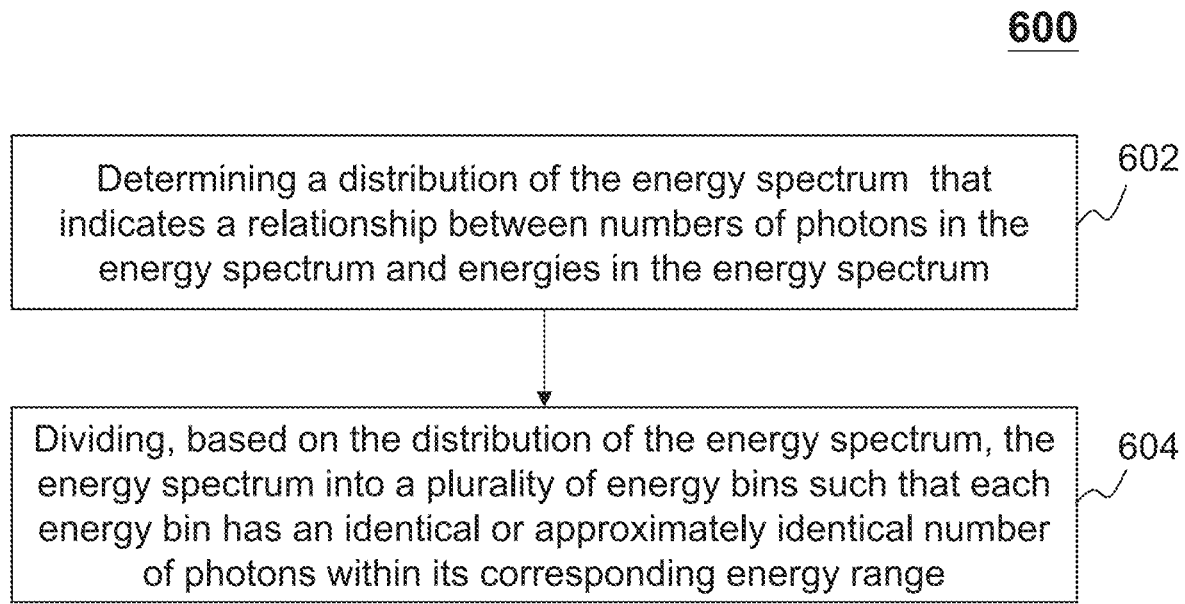
FIG. 6 is a flowchart illustrating an exemplary process for dividing an energy spectrum of X-rays according to some embodiments of the present disclosure.

FIG. 6 is a flowchart illustrating an exemplary process 600 for dividing an energy spectrum of X-rays according to some embodiments of the present disclosure. In some embodiments, at least part of the process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order of the operations of the process 600 as illustrated in FIG. 6 and described below is not intended to be limiting. In some embodiments, the operation 502 may be achieved according to the process 600.

In 602, the processing device 140 (e.g., the energy spectrum dividing module 410) may determine a distribution of the energy spectrum of the X-rays that indicates a relationship between numbers of photons in the energy spectrum and energies in the energy spectrum.

In some embodiments, as described elsewhere in this disclosure (e.g., FIG. 5 and the relevant descriptions), the energy spectrum of the X-rays may vary over the spatial positions, and thus different regions of the projection image may each correspond to a distinctive energy spectrum. The distribution of the energy spectrum may be determined based on at least one of the distinctive energy spectra. For example, the distribution of the energy spectrum may be represented as a distribution function derived from one of the distinctive energy spectra. As another example, the distribution of the energy spectrum may be represented as a weighted average of distribution functions that are derived from at least two of the distinctive energy spectra. More descriptions regarding the distribution function(s) and the distribution of the energy spectrum may be found elsewhere in the present disclosure. See, e.g., FIG. 7 and relevant descriptions thereof.

In 604, the processing device 140 (e.g., the energy spectrum dividing module 410) may divide, based on the distribution of the energy spectrum, the energy spectrum into a plurality of energy bins such that each energy bin has an identical or approximately identical number of photons within its corresponding energy range. As used herein, if two numbers are approximately identical, it may denote that the difference between the two numbers is within a threshold. For example, the threshold may be a preset number, e.g., $10^2$, $10^3$, $10^4$, or any other suitable value. As another example, the threshold may be a ratio of one of the two numbers, wherein the ratio may be 1%, 3%, 5%, 10%, 20%, or any other suitable value.

In some embodiments, the distribution of the energy spectrum may include a cumulative distribution function (CDF) of the energy spectrum, and the processing device 140 (e.g., the energy spectrum dividing module 410) may divide the energy spectrum based on the cumulative distribution function. In some embodiments, the CDF of the energy spectrum, whose abscissa represents the spectrum energy and ordinate represents a representation of the number of photons, may be determined by integrating the energy spectrum with respect to energy. Under the circumstance that the energy spectrum is spatially varying, the CDF of the energy spectrum may denote a CDF of a distinctive energy spectrum of the spatially-varying energy spectrum, which may be calculated by integrating the distinctive energy spectrum with respect to the energy. Alternatively, the CDF of the energy spectrum may denote an "average" representation of the CDFs of two or more distinctive energy spectra of the spatially-varying energy spectrum, and can be calculated by calculating an area-weighted average of the CDFs of the two or more distinctive energy spectra. More descriptions regarding the CDF may be found elsewhere in the present disclosure. See, e.g., FIG. 7 and relevant descriptions thereof. If, for example, 10 energy bins are to be created, 9 equi-spaced ordinates may be selected from the CDF, i.e. 0.1, 0.2, 0.3, 0.4, 0.5, 0.6, 0.7, 0.8, 0.9. By means of inverse look-up of the CDF abscissa points, this yields 9 energy bin limits, with each energy bin containing approximately or exactly one tenth of photons present in the X-rays.

Figure 11:
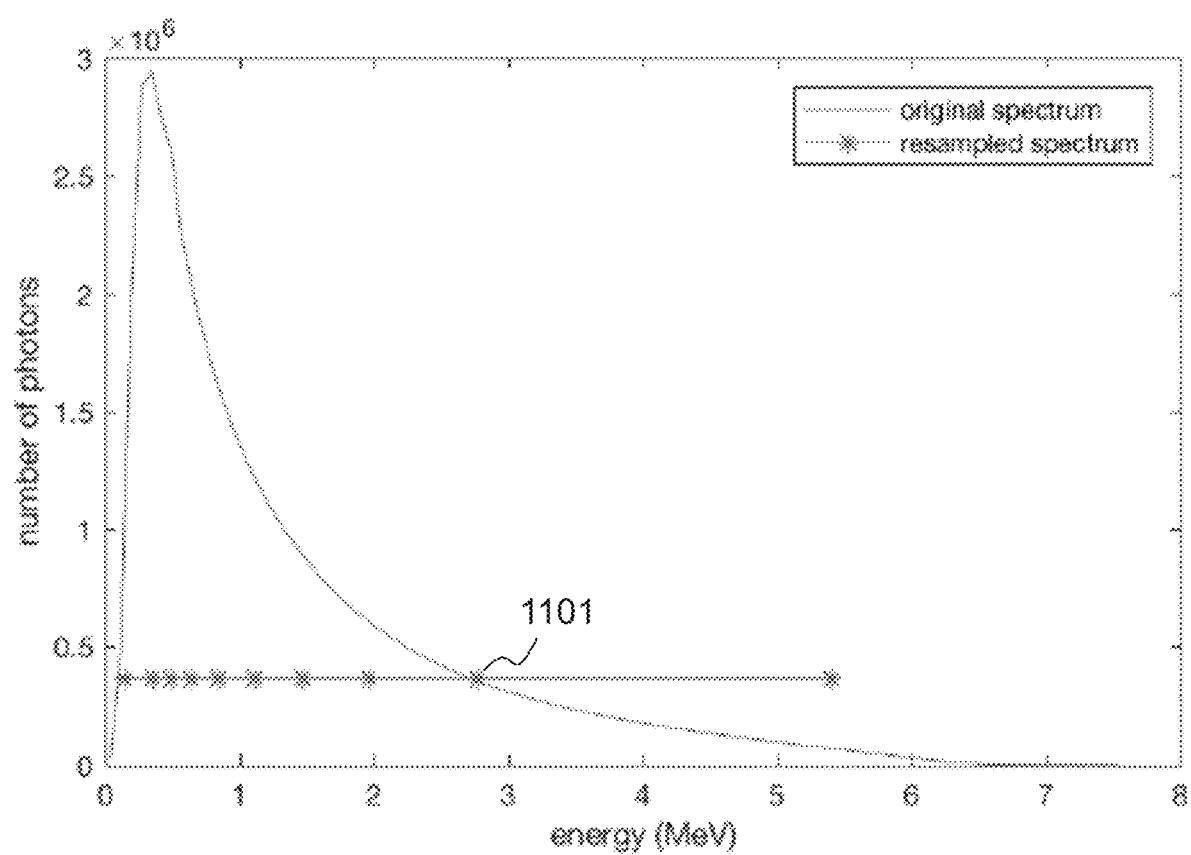
FIG. 11 is a schematic diagram illustrating an exemplary energy spectrum divided into different energy bins according to some embodiments of the present disclosure.

For illustration purposes, FIG. 11 shows an exemplary energy spectrum (e.g., a distinctive energy spectrum corresponding to a region of the projection image) with values of spectrum energy represented in the abscissa and numbers of photons represented in the ordinate. A plurality of points 1101 indicated by the sign "*" represent the division of the energy spectrum. Specifically, the abscissa coordinate of each point 1101 represents an energy bin limit. In certain embodiments, the points 1101 are selected such that the number of photons in each energy bin is identical or approximately identical.

It should be noted that the above descriptions of the process 600 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 600 may include one or more other operations. However, those variations and modifications also fall within the scope of the present disclosure.

FIG. 7 is a flowchart illustrating an exemplary process 700 for determining a distribution of energy spectrum according to some embodiments of the present disclosure. In some embodiments, at least part of the process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order of the operations of the process 700 as illustrated in FIG. 7 and described below is not intended to be limiting. In some embodiments, the operation 604 may be achieved according to the process 700.

In 702, the processing device 140 (e.g., the energy spectrum dividing module 410) may determine, from the spatially-varying energy spectrum of the X-rays, at least one distinctive energy spectrum that corresponds to at least one region of the projection image. In some embodiments, the at least one distinctive energy spectrum may include a plurality of distinctive energy spectra corresponding to different regions of the projection image. As used in the present disclosure, the energy spectrum of the X-rays varying with respect to different regions of the projection image may be deemed as including a plurality of different energy spectra corresponding to different regions of the projection image, and each of the plurality of different energy spectra may be further regarded as a distinctive energy spectrum.

Figure 10A:
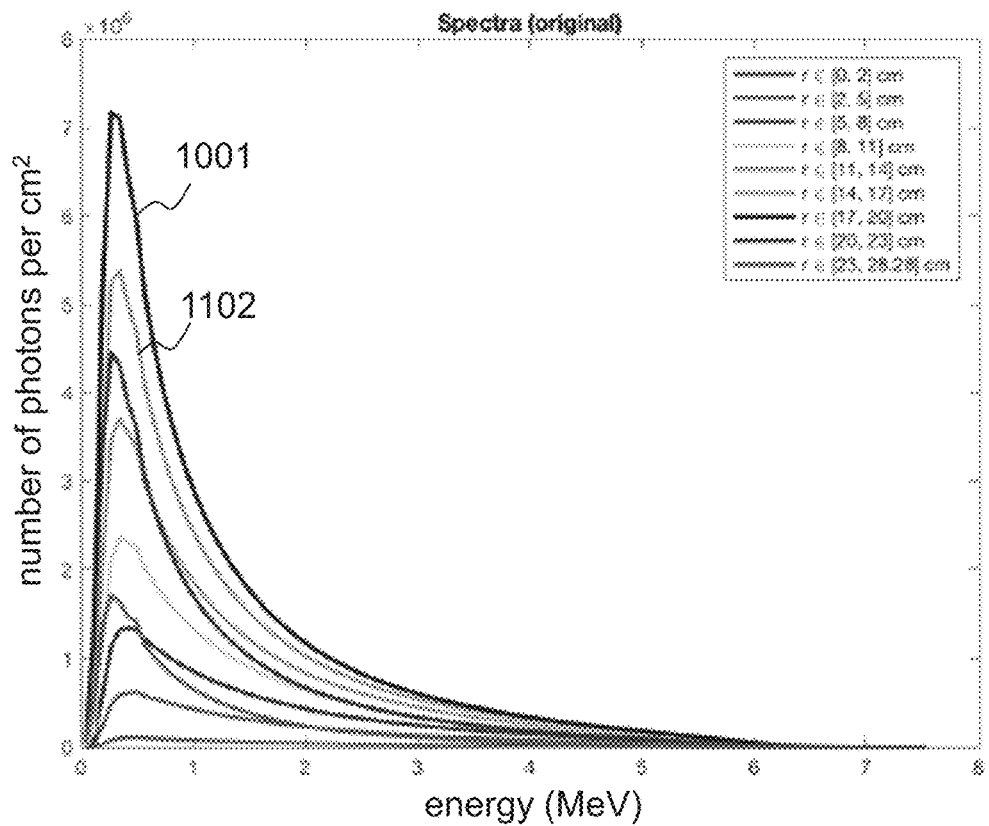
FIG. 10a is a schematic diagram illustrating a plurality of energy spectra according to some embodiments of the present disclosure.
Figure 10B:
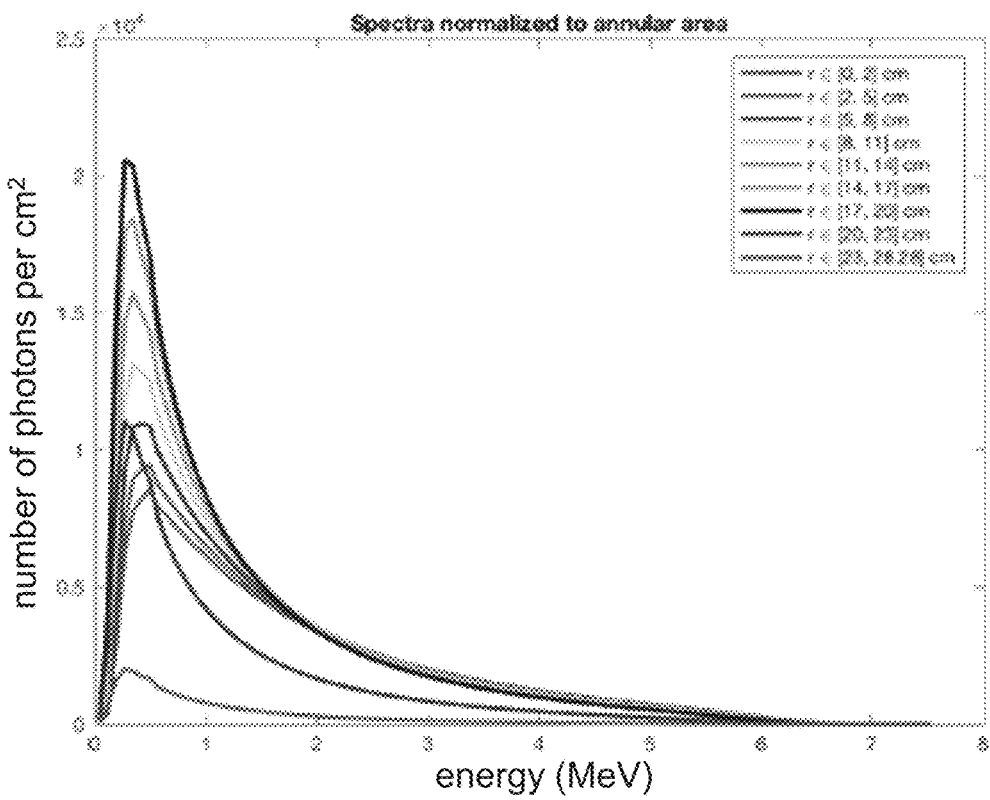
FIG. 10b is a schematic diagram illustrating a plurality of normalized energy spectra according to some embodiments of the present disclosure.

For illustration purposes, a plurality of distinctive energy spectra is shown in FIG. 10a. The plurality of distinctive energy spectra jointly forms the spatially-varying energy spectrum, and each of the plurality of distinctive energy spectra corresponds to an annular ring of a projection image. For example, the distinctive energy spectrum 1101 is the regional energy spectrum of a first annular ring radially ranging from 17 cm to 20 cm, and the distinctive energy spectrum 1102 is the regional energy spectrum of a second annular ring radially ranging from 14 cm to 17 cm, which is adjoining to the first annular ring. The abscissa of the distinctive energy spectra denotes the spectrum energy, and the ordinate of the distinctive energy spectra denotes the numbers of photon per $cm^2$ within the corresponding region of the distinctive energy spectrum. In FIG. 10b, the normalized energy spectra of the plurality of distinctive energy spectra in FIG. 10a is shown. Compared to FIG. 10a, each of the distinctive energy spectra is normalized to the area of its corresponding region. Therefore, in FIG. 10b, the ordinate of the distinctive energy spectra denotes the total numbers of photons within the corresponding region of the distinctive energy spectrum.

In 704, the processing device 140 (e.g., the energy spectrum dividing module 410) may determine a CDF for each of the plurality of distinctive energy spectra, each CDF corresponding to one of the different regions of the projection image.

In some embodiments, supposing that the projection image is divided into K regions indicated as $\Omega_k$, k=1, 2, . . . , K, the CDF corresponding to each region may be determined based on following formula:

$$S_k(E) = \frac{\int_0^E dE\, s_k(E)}{\int_0^\infty dE\, s_k(E)}, \quad (4)$$

where $s_k(E)$ is a distinctive energy spectrum that irradiates the region $\Omega_k$. In some embodiments, the distinctive energy spectrum $s_k(E)$ may be denoted as the curve shown in FIG. 10a or FIG. 10b. In some alternative embodiments, the distinctive energy spectrum $s_k(E)$ may be determined by, for example, histogramming photon energies within the region $\Omega_k$.

In 706, the processing device 140 (e.g., the energy spectrum dividing module 410) may determine an area of each of the different regions of the projection image. In some embodiments, the area of each of the different regions of the projection image may be the actual area of the corresponding region, or may be a weighted area determined based on a weighting factor and the actual area of that region. More descriptions regarding the determination of the area of a region of the projection image may be found elsewhere in the present disclosure. See, e.g., FIG. 8 and the descriptions thereof.

In 708, the processing device 140 (e.g., the energy spectrum dividing module 410) may weight each of the plurality of CDFs by its corresponding area. A plurality of weighted CDFs corresponding to the plurality of energy spectra may be obtained by, for example, multiplying each CDF by its corresponding area.

In 710, the processing device 140 (e.g., the energy spectrum dividing module 410) may determine the distribution of the energy spectrum based on the weighted CDFs. In some embodiments, the distribution of the energy spectrum may be determined as an "average" representation of the CDFs.

For illustration purposes, the distribution of the energy spectrum may be determined as follows:

$$\bar{S}[E] = \frac{\sum_{k=1}^{K} S_k[E]|\Omega_k|}{\sum_{k=1}^{K} |\Omega_k|}, \quad (5)$$

where $|\Omega_k|$ denotes the area of region $\Omega_k$, and $S_k[E]$ is a CDF of the distinctive energy spectrum corresponding to region $\Omega_k$. The $S_k[E]$ may be determined according to formula (4).

It should be noted that the above descriptions of the process 700 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 700 may include one or more other operations. However, those variations and modifications also fall within the scope of the present disclosure.

Figure 8:
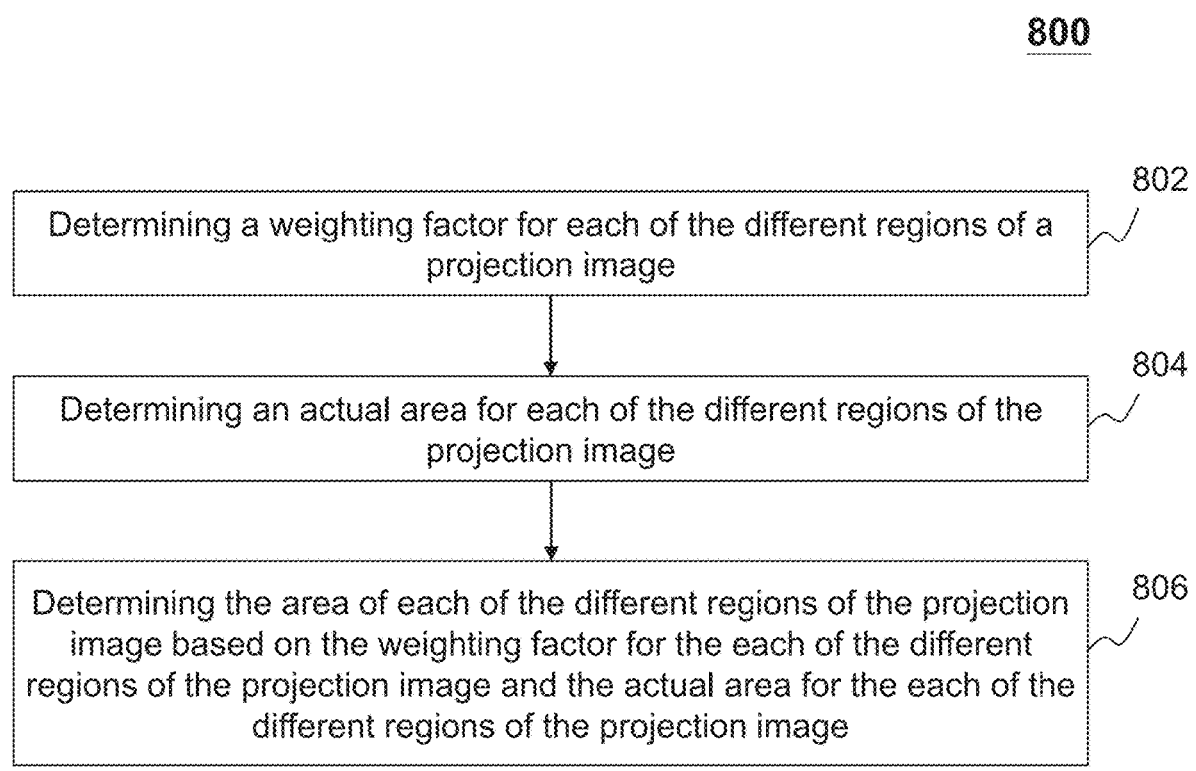
FIG. 8 is a flowchart illustrating an exemplary process for determining an area of each of different regions of a projection image according to some embodiments of the present disclosure.

FIG. 8 is a flowchart illustrating an exemplary process 800 for determining an area of each of different regions of projection image according to some embodiments of the present disclosure. In some embodiments, at least part of the process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order of the operations of the process 800 as illustrated in FIG. 7 and described below is not intended to be limiting. In some embodiments, the operation 706 may be achieved according to the process 800.

In 802, the processing device 140 (e.g., the energy spectrum dividing module 410) may determine a weighting factor for each of the different regions of a projection image.

In some embodiments, the weighting factor for each of the different regions of the projection image may be associated with various factors. Merely by way of example, the weighting factor for one region may be associated with the position of the region. For example, if a region is closer to the center of the projection image, the region may be regarded as having a higher importance than the regions further away from the center of the projection image, and may be assigned with a higher weighting factor. In this situation, the center region of the projection image may be assigned with the highest weighting factor.

In some embodiments, the weighting factor for each of the different regions of the projection image may be determined based on a plurality of techniques such as a weighting formula, a weighting algorithm, a pre-trained weighting model, a pre-determined weighting rule, or the like, or any combination thereof.

In 804, the processing device 140 (e.g., the energy spectrum dividing module 410) may determine an actual area for each of the different regions of the projection image. In a specific embodiment, as described elsewhere in the disclosure, the projection image may be divided into two or more annular rings. In this situation, the actual area of the region $\Omega_k$ may be determined by:

$$|\Omega_k| = \pi(r_k^2 - r_{k-1}^2), \quad (6)$$

where $|\Omega_k|$ is the actual area of the region $\Omega_k$, $r_k$ is the outer radius of the region $\Omega_k$, and $r_{k-1}$ is the inner radius of the region $n_k$.

In 806, the processing device 140 (e.g., the energy spectrum dividing module 410) may determine the area of each of the different regions of the projection image based on the weighting factor for the each of the different regions of the projection image and the actual area for the each of the different regions of the projection image. For example, the processing device 140 (e.g., the energy spectrum dividing module 410) may determine the area of the each of the different regions of the projection image by multiplying the actual area for the each of the different regions of the projection image with the corresponding weighting factor.

It should be noted that the above descriptions of the process 800 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, one or more operations described in the process 800 may be omitted. For example, the processing device 140 (e.g., the energy spectrum dividing module 410) may determine the area of the each of the different regions of the projection image directly without determining the actual area for the each of the different regions of the projection image. In some embodiments, the process 800 may include one or more other operations. However, those variations and modifications also fall within the scope of the present disclosure.

Figure 9:
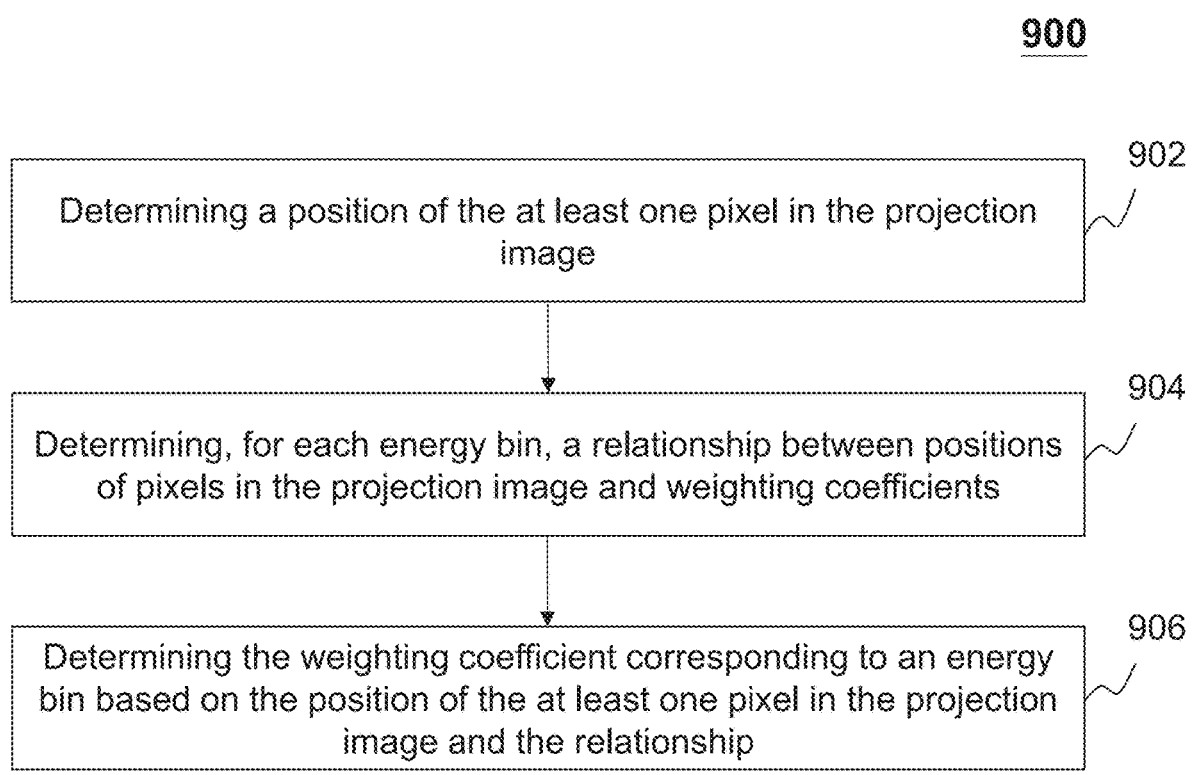
FIG. 9 is a flowchart illustrating an exemplary process for determining a weighting coefficient corresponding to an energy bin according to some embodiments of the present disclosure.

FIG. 9 is a flowchart illustrating an exemplary process 900 for determining a weighting coefficient corresponding to an energy bin according to some embodiments of the present disclosure In some embodiments, at least part of the process 900 may be performed by the processing device 140 (implemented in, for example, the computing device 200 shown in FIG. 2). For example, the process 900 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 900 may be accomplished with one or more additional operations not described, and/or without one or more of the operations discussed. Additionally, the order of the operations of the process 900 as illustrated in FIG. 9 and described below is not intended to be limiting. In some embodiments, the operation 508 may be achieved according to the process 900.

In 902, the processing device 140 (e.g., the weighting coefficient determination module 430) may determine a position of the at least one pixel in the projection image.

In some embodiments, the projection image may be located in a specific coordinate system. The position of the at least one pixel in the projection image may be represented by one or more coordinates in the specific coordinate system. For example, the position of the at least one pixel in the projection image may be represented by a set of Cartesian coordinates, which may include a horizontal position and/or a vertical position. For another example, the position of the at least one pixel in the projection image may be represented by a set of polar coordinates, which may include a radial position and/or a circumferential position. Additionally or alternatively, the origin of the specific coordinate system may be set at any position, e.g., the center of the projection image.

In 904, the processing device 140 (e.g., the weighting coefficient determination module 430) may determine, for each energy bin, a relationship between positions of pixels in the projection image and weighting coefficients.

In some embodiments, the relationship between positions of pixels in the projection image and weighting coefficients may be represented by a specific function. The specific function may be of any type, such as, a linear function, a nonlinear function. It shall be noted that any other form that can indicate the relationship between positions of pixels in the projection image and weighting coefficients may also be used herein, which is be limited in the disclosure.

In some embodiments, for each energy bin, to determine the relationship between positions of pixels in the projection image and weighting coefficients, the processing device 140 (e.g., the weighting coefficient determination module 430) may determine a representative weighting coefficient corresponding to the energy bin for each of the different regions of the projection image. For each of the different regions of the projection image, its representative weighting coefficient may relate to the count of photons that are within the energy range of the energy bin.

For illustration purpose, a representative spectrum for each of the different regions of the projection image may be determined as a representative weighting coefficient for the each of the different regions of the projection image. For example, supposing that a projection image is divided into K regions with successive radial limits of $[r_k, r_{k+1})$ for $r_0, r_1, \ldots, r_K, r_{k+1} > r_k$, a representative spectrum for the region $\Omega_k$ may be expressed as:

$$S_k[n] = \int_{E_{n-1}}^{E_n} dE s_k(E) \; n=1,2,\ldots,N, \qquad (7)$$

where En and En−1 represent the two energy limits of the nth energy bin.

Then, the representative spectrum $S_k[n]$ may be used as the representative weighting coefficient of a specific position within the region $\Omega_k$, e.g., at a mean radius of the region $\Omega_k$.

Further, the processing device 140 may obtain the representative weighting coefficients for all of the different regions of the projection image. For convenience, each of the representative weighting coefficient may correspond to the same specific position (e.g., the mean radius) of the corresponding region. It shall be noted that the specific position which is assigned with the representative weighting coefficient may be other positions different from the mean radius, e.g., the outer radius, the inner radius, which is not limited in the disclosure. Moreover, the processing device 140 (e.g., the weighting coefficient determination module 430) may determine a function by fitting the representative weighting coefficients of the different regions at the specific positions. For example, the processing device 140 (e.g., the weighting coefficient determination module 430) may fit the representative weighting coefficients with an interpolation operation. Specifically, the processing device 140 (e.g., the weighting coefficient determination module 430) may interpolate $S_k[n]$ for a specific pixel with a specific radial distance with respect to the center of the projection image. Then, a fitted interpolating function may be determined, which may be further used to determine a weighting coefficient $\omega_n[u, v]$ of the pixel [u, v] corresponding to the nth energy bin.

In some embodiments, the relationship may be such that the weighting coefficients corresponding to the energy bin change continuously with respect to the positions of the pixels in the projection image. For illustration purposes, in FIG. 12a, a first weighting map that shows the weighting coefficients at different positions within the projection image is shown. The first weighting map shows the relationship between positions of pixels in the projection image and weighting coefficients corresponding to a $2^{nd}$ energy bin with the energy ranging from 03503 MeV to 0.4846 MeV. The gray value at each point represents the weighting coefficient thereof. In FIG. 12b, a second weighting map corresponding to a different energy bin is shown. The second weighting map shows the relationship between positions of pixels in the projection image and weighting coefficients corresponding to a $5^{th}$ energy bin with the energy ranging from 0.8480 MeV to 1.1104 MeV. It can be noted that, in both of the FIG. 12a and FIG. 12b, the weighting coefficients vary continuously over the projection image, while the first weighting map and the second weighting map may correspond to different functions. Specifically, a same pixel in the projection image may have two different weighting coefficients corresponding to the two different energy bins. For example, for the $2^{nd}$ energy bin, the center pixel has a weighting coefficient whose value is approximate to 0.058, and for the $5^{th}$ energy bin, the center pixel has a weighting coefficient whose value is approximate to 0.093.

In 906, the processing device 140 (e.g., the weighting coefficient determination module 430) may determine the weighting coefficient corresponding to an energy bin based on the position of the at least one pixel in the projection image and the relationship. For example, the weighting coefficient corresponding to the energy bin may be determined based on a radial distance of the at least one pixel with respect to the center of the projection image, and the function that represents the relationship as described in the operation 904.

It should be noted that the above descriptions of the process 900 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 900 may include one or more other operations. However, those variations and modifications also fall within the scope of the present disclosure.

FIG. 10a is a schematic diagram illustrating a plurality of distinctive energy spectra within a spatially-varying energy spectrum according to some embodiments of the present disclosure. As shown in FIG. 10a, the plurality of distinctive energy spectra corresponds to different regions of a projection image, wherein 9 regions are listed with their radial limits at r ∈ [0, 2)cm, r ∈ [2, 5)cm, . . . , r ∈ [23, 28.28)cm, respectively. The abscissa of the distinctive energy spectra denotes the spectrum energy, and the ordinate of the distinctive energy spectra denotes the numbers of photon per $cm^2$ within the corresponding region of the distinctive energy spectrum.

In comparison, FIG. 10b is a schematic diagram illustrating a plurality of distinctive energy spectra normalized to area of regions according to some embodiments of the present disclosure. As shown in FIG. 10b, each of the distinctive energy spectra is normalized to the area of its corresponding region, and the ordinate of the distinctive energy spectra denotes the total numbers of photons within the corresponding region of each distinctive energy spectrum.

FIG. 11 is a schematic diagram illustrating an exemplary energy spectrum divided into different energy bins according to some embodiments of the present disclosure. As shown in FIG. 11, an original energy spectrum is expressed with values of spectrum energy represented in the abscissa, and numbers of photons represented in the ordinate. The original energy spectrum is divided (or resampled), according to the abscissa coordinates of the points indicated by the sign "*", into 10 energy bins with respective energy limits. In each of the 10 energy bins, the counts of photons is identical or approximately identical.

Figure 12A:
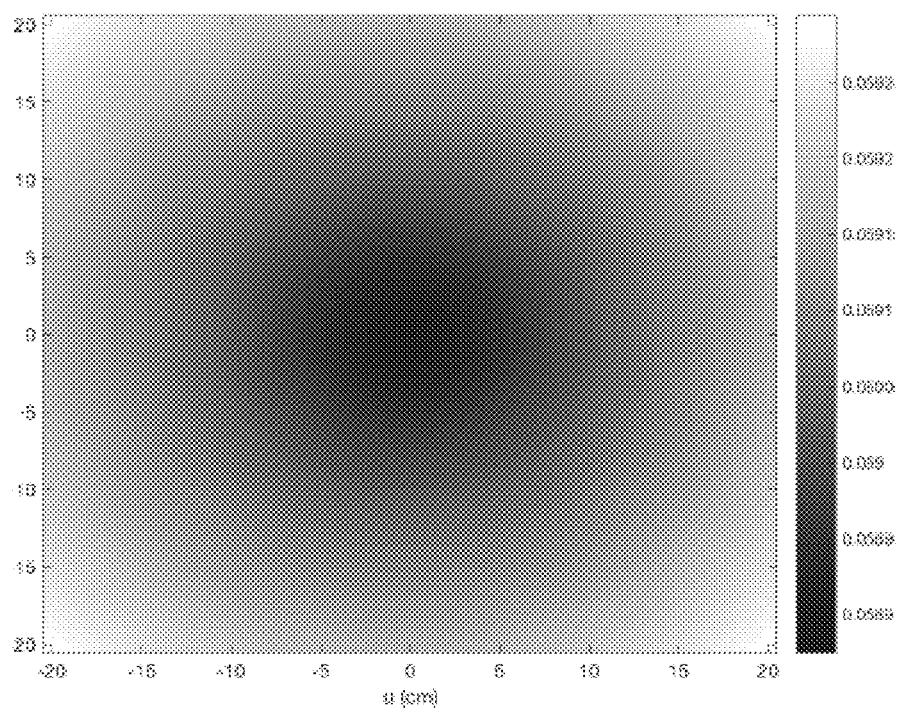
FIG. 12a is a schematic diagram illustrating a weighting map according to some embodiments of the present disclosure.
Figure 12B:
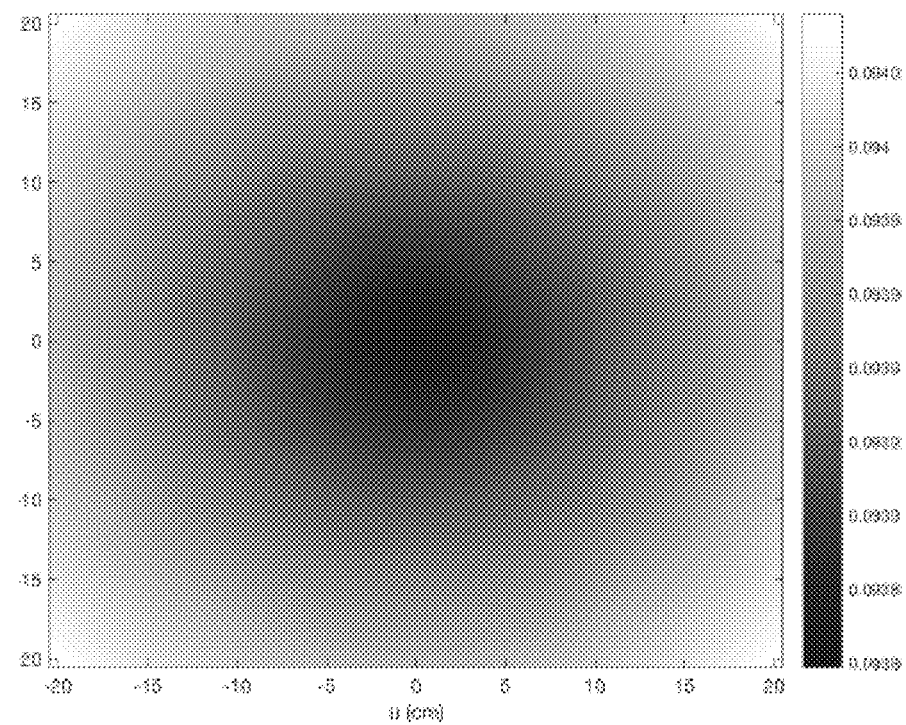
FIG. 12b is a schematic diagram illustrating a weighting map according to some embodiments of the present disclosure.

FIG. 12a is a schematic diagram illustrating a weighting map according to some embodiments of the present disclosure. As shown in FIG. 12a, the weighting map indicates variations of weighting coefficients corresponding to the $2^{nd}$ energy bin within the energy range [0.3503, 0.4846)MeV. The weighting coefficients $\omega_2[u, v]$ change continuously with respect to positions of pixels in the projection image.

FIG. 12b is a schematic diagram illustrating a weighting map according to some embodiments of the present disclosure. As shown in FIG. 12a, the weighting map indicates variations of weighting coefficients corresponding to the $5^{th}$ energy bin within the energy range [0.8480, 1.1104)MeV. The weighting coefficients $\omega_5[u, v]$ change continuously with respect to positions of pixels in the projection image.

Figure 13:
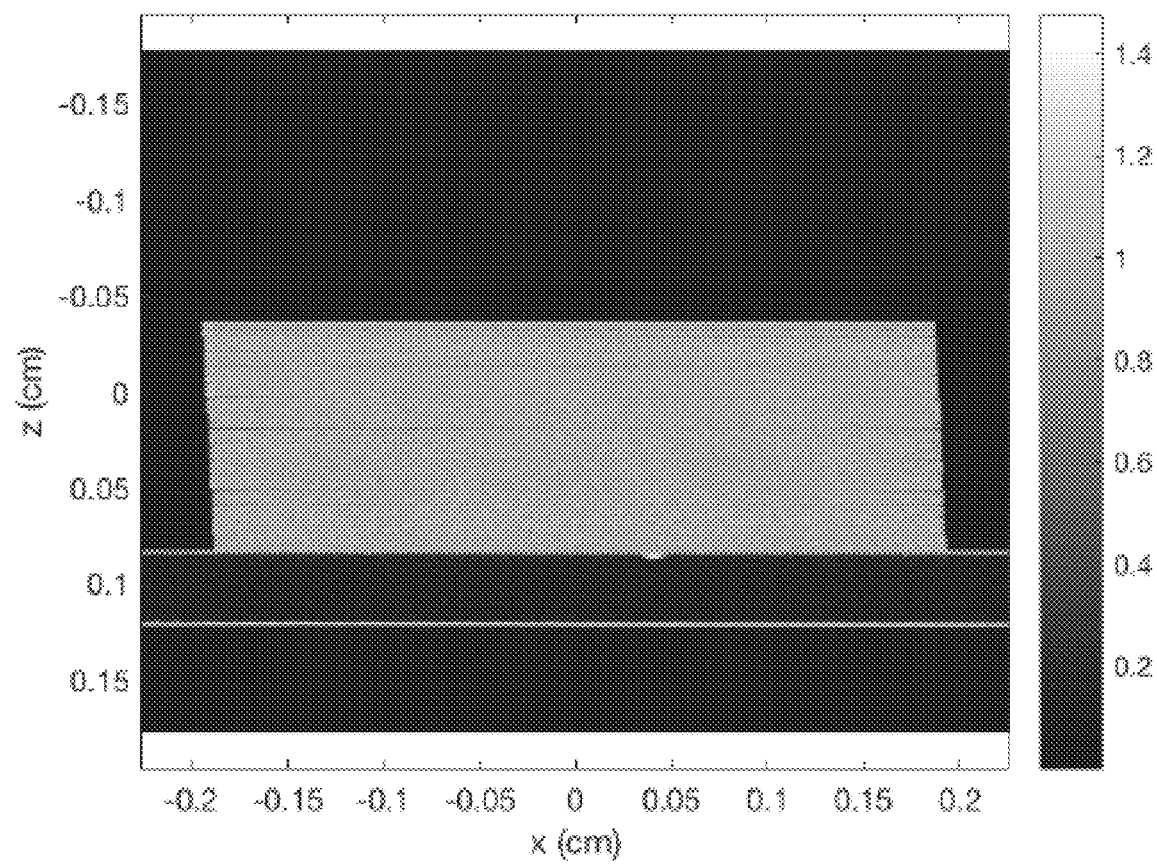
FIG. 13 is a schematic diagram illustrating water-equivalent slabs according to some embodiments of the present disclosure.

FIG. 13 is a schematic diagram illustrating water-equivalent slabs according to some embodiments of the present disclosure. As shown in FIG. 13, water-equivalent slabs having a total thickness of 15 cm is placed on a treatment couch (e.g., the table 114 in the imaging devices 110). An X-ray beam in 6 MV is propagated through the water-equivalent slabs along the positive z-axis to obtain projection images.

Figure 14A:
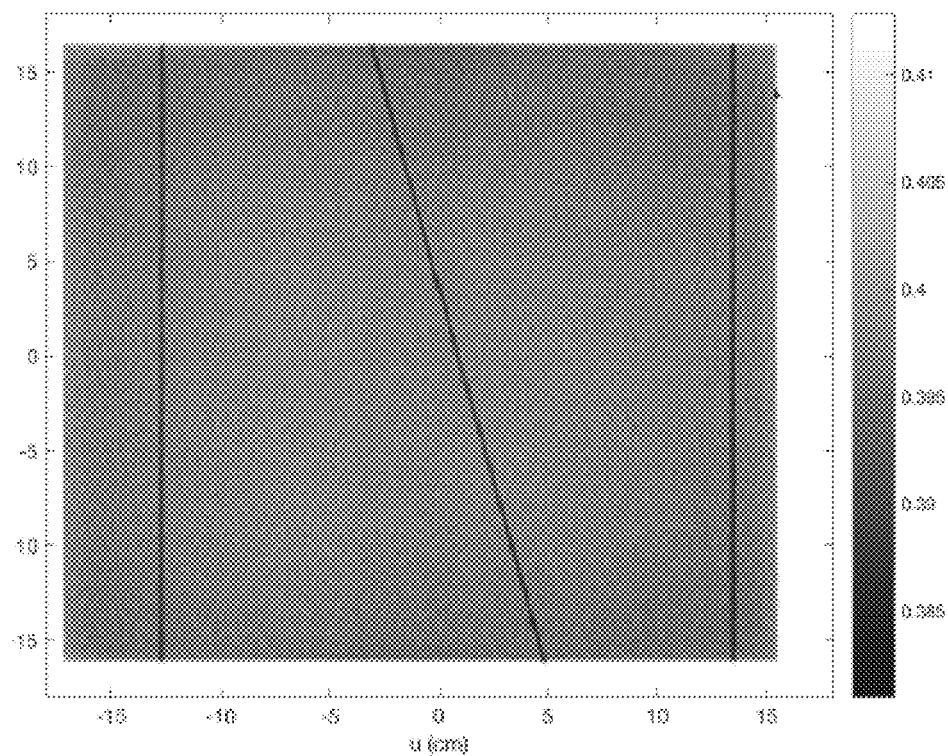
FIG. 14a is a schematic diagram illustrating a projection image synthesized from a radiation source with spatially-varying spectrum according to some embodiments of the present disclosure.

FIG. 14a is a schematic diagram illustrating a projection image synthesized from radiation source with spatially-varying spectrum according to some embodiments of the present disclosure. As shown in FIG. 14a, based on methods and systems described in the disclosure, the projection image is synthesized from the X-ray beam in 6 MV used in FIG. 13 through the water-equivalent slabs along the positive z-axis. The projection image is shown in units of primary transmission. The vertical and oblique dark lines in the projection image are wires embedded in the treatment couch (e.g., the table 114 in the imaging devices 110). The projection image is viewed using a limited intensity windows of ±4%, and there is no visible radial artifact at radial zone on the projection image.

Figure 14B:
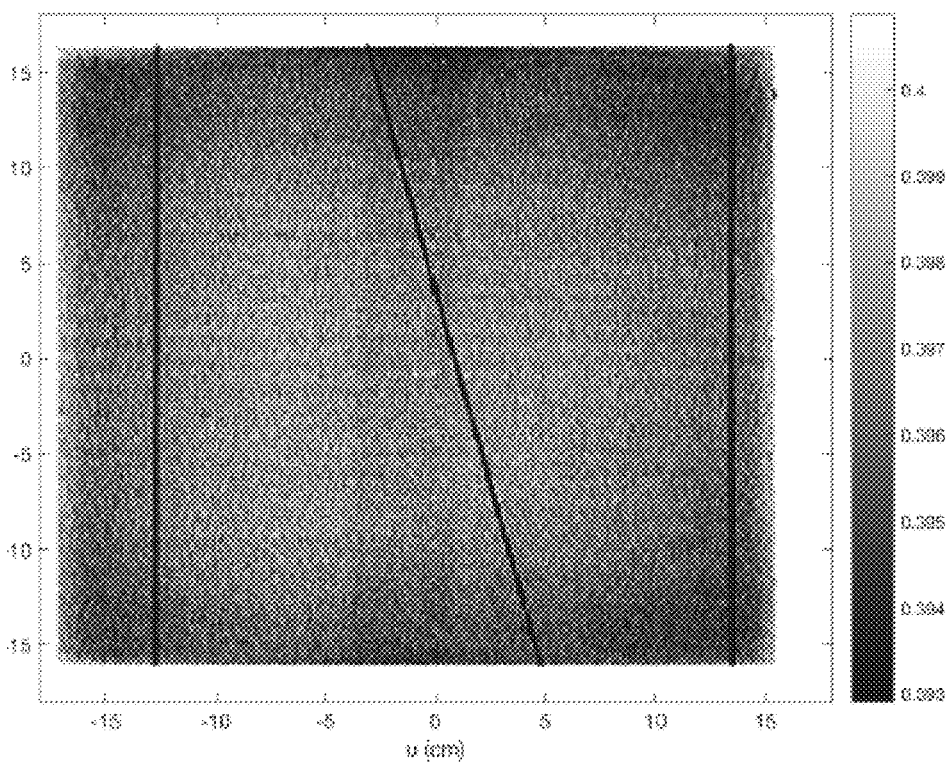
FIG. 14b is a schematic diagram illustrating a projection image synthesized from a radiation source with spatially-varying spectrum according to some embodiments of the present disclosure.

FIG. 14b is a schematic diagram illustrating a projection image synthesized from radiation source with spatially-varying spectrum according to some embodiments of the present disclosure. As shown in FIG. 14b, based on methods and systems described in the disclosure, the projection image is synthesized from the X-ray beam in 6 MV used in FIG. 13 through the water-equivalent slabs along the positive z-axis. The projection image is shown in units of primary transmission. The vertical and oblique dark lines in the projection image are wires embedded in the treatment couch (e.g., the table 114 in the imaging devices 110). The projection image is viewed using a limited intensity windows of ±1% and there is no visible radial artifact at radial zone on the projection image.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In dosing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for synthesizing a projection image, the projection image representing a subject or object irradiated by X-rays from a radiation source, the method comprising:
   dividing an energy spectrum of the X-rays into one or more energy bins, the energy spectrum of the X-rays varying with respect to different regions of the projection image, each of the one or more energy bins corresponding to an energy range;
   for at least one pixel of the projection image,
      for each energy bin of the one or more energy bins,
         determining a projection value of the at least one pixel indicating a transmission projection of X-rays corresponding to the at least one pixel and having an energy within the corresponding energy range of the energy bin;
         determining a weighting coefficient corresponding to the energy bin based on a variation of the energy spectrum of the X-rays between the different regions of the projection image; and
         determining a weighted projection value of the at least one pixel based on the projection value of the at least one pixel and the weighting coefficient corresponding to the energy bin; and
      determining a pixel value of the at least one pixel based on the weighted projection values of the at least one pixel that correspond to all of the one or more energy bins.

2. The method of claim 1, wherein dividing an energy spectrum of the X-rays into one or more energy bins comprises:
   determining a distribution of the energy spectrum that indicates a relationship between numbers of photons in the energy spectrum and energies in the energy spectrum; and
   dividing the energy spectrum into a plurality of energy bins based on the distribution of the energy spectrum such that each energy bin has an approximately identical number of photons within its corresponding energy range.

3. The method of claim 2, wherein determining a distribution of the energy spectrum that indicates a relationship between numbers of photons in the energy spectrum and energies in the energy spectrum comprises:
   determining at least one distinctive energy spectrum that corresponds to at least one region of the projection image; and
   determining the distribution of the energy spectrum based on a cumulative distribution function (CDF) of the at least one distinctive energy spectrum.

4. The method of claim 3, wherein the at least one distinctive energy spectrum includes a plurality of distinctive energy spectra corresponding to different regions of the projection image, wherein determining the distribution of the energy spectrum based on a cumulative distribution function (CDF) of the at least one distinctive energy spectrum comprises:
   determining a CDF for each of the plurality of distinctive energy spectra, each CDF corresponding to one of the different regions of the projection image; and
   determining the distribution of the energy spectrum based on an area-weighted mean of the plurality of CDFs corresponding to the plurality of distinctive energy spectra.

5. The method of claim 4, wherein determining the distribution of the energy spectrum based on an area-weighted mean of the plurality of CDFs corresponding to the plurality of distinctive energy spectra comprises:
   determining an area of each of the different regions of the projection image;
   weighting each of the plurality of CDFs by its corresponding area; and
   determining the distribution of the energy spectrum based on the weighted CDFs.

6. The method of claim 5, wherein determining an area of each of the different regions of the projection image comprises:
   determining a weighting factor for the each of the different regions of the projection image;
   determining an actual area for the each of the different regions of the projection image; and
   determining the area of the each of the different regions of the projection image based on the weighting factor for the each of the different regions of the projection image and the actual area for the each of the different regions of the projection image.

7. The method of claim 1, wherein determining a projection value of the at least one pixel indicating a transmission projection of X-rays corresponding to the at least one pixel and having an energy within the corresponding energy range of the energy bin comprises:
   determining a line integral of an attenuation coefficient along a direction of the X-rays corresponding to the at least one pixel and having the energy within the corresponding energy range of the energy bin.

8. The method of claim 7, wherein the attenuation coefficient corresponds to an average energy of the energy bin.

9. The method of claim 1, wherein determining a weighting coefficient corresponding to the energy bin based on a variation of the energy spectrum of the X-rays with respect to the different regions of the projection image comprises:
   determining a position of the at least one pixel in the projection image;
   determining a relationship between positions of pixels in the projection image and weighting coefficients corresponding to the energy bin; and
   determining the weighting coefficient corresponding to the energy bin based on the position of the at least one pixel in the projection image and the relationship.

10. The method of claim 9, wherein a position of a pixel in the projection image includes a radial distance of the at least one pixel with respect to a center of the projection image.

11. The method of claim 9, comprising:
   determining, for each of the different regions of the projection image, a representative weighting coefficient corresponding to the energy bin; and
   determining a function representing the relationship by fitting the representative weighting coefficients of the different regions of the projection image.

12. The method of claim 11, wherein the representative weighting coefficient corresponding to the energy bin for each of the different regions of the projection image relates to a count of photons that are within the energy range of the energy bin and correspond to the each of the different regions of the projection image.

13. The method of claim 9, wherein the relationship is such that the weighting coefficients corresponding to the energy bin change continuously with respect to the positions of the pixels in the projection image.

14. The method of claim 1, wherein the weighting coefficient corresponding to each energy bin is a weighting of a basis set that approximates the energy spectrum of the X-rays over the projection image.

15. A system for synthesizing a projection image, comprising:
   at least one storage medium including a set of instructions; and
   at least one processor in communication with the at least one storage medium, wherein when executing the instructions, the at least one processor is configured to direct the system to perform operations including:
      dividing an energy spectrum of the X-rays into one or more energy bins, the energy spectrum of the X-rays varying with respect to different regions of the projection image, each of the one or more energy bins corresponding to an energy range;
      for at least one pixel of the projection image,
      for each energy bin of the one or more energy bins,
         determining a projection value of the at least one pixel indicating a transmission projection of X-rays corresponding to the at least one pixel and having an energy within the corresponding energy range of the energy bin;
         determining a weighting coefficient corresponding to the energy bin based on a variation of the energy spectrum of the X-rays between the different regions of the projection image; and
         determining a weighted projection value of the at least one pixel based on the projection value of the at least one pixel and the weighting coefficient corresponding to the energy bin; and
      determining a pixel value of the at least one pixel based on the weighted projection values of the at least one pixel that correspond to all of the one or more energy bins.

16. The system of claim 15, wherein dividing an energy spectrum of the X-rays into one or more energy bins comprises:
   determining a distribution of the energy spectrum that indicates a relationship between numbers of photons in the energy spectrum and energies in the energy spectrum; and
   dividing the energy spectrum into a plurality of energy bins based on the distribution of the energy spectrum such that each energy bin has an approximately identical number of photons within its corresponding energy range.

17. The system of claim 16, wherein determining a distribution of the energy spectrum that indicates a relationship between numbers of photons in the energy spectrum and energies in the energy spectrum comprises:
   determining at least one distinctive energy spectrum that corresponds to at least one region of the projection image; and
   determining the distribution of the energy spectrum based on a cumulative distribution function (CDF) of the at least one distinctive energy spectrum.

18. The system of claim 17, wherein the at least one distinctive energy spectrum includes a plurality of distinctive energy spectra corresponding to different regions of the projection image, wherein determining the distribution of the energy spectrum based on a cumulative distribution function (CDF) of the at least one distinctive energy spectrum comprises:

determining a CDF for each of the plurality of distinctive energy spectra, each CDF corresponding to one of the different regions of the projection image; and determining the distribution of the energy spectrum based on an area-weighted mean of the plurality of CDFs corresponding to the plurality of distinctive energy spectra.

19. The system of claim 15, wherein determining a projection value of the at least one pixel indicating a transmission projection of X-rays corresponding to the at least one pixel and having an energy within the corresponding energy range of the energy bin comprises:

determining a line integral of an attenuation coefficient along a direction of the X-rays corresponding to the at least one pixel and having the energy within the corresponding energy range of the energy bin.

20. The system of claim 15, wherein determining a weighting coefficient corresponding to the energy bin based on a variation of the energy spectrum of the X-rays with respect to the different regions of the projection image comprises:

determining a position of the at least one pixel in the projection image;

determining a relationship between positions of pixels in the projection image and weighting coefficients corresponding to the energy bin; and determining the weighting coefficient corresponding to the energy bin based on the position of the at least one pixel in the projection image and the relationship.

* * * * *